United States Patent [19]

Lovin et al.

[11] Patent Number: 5,486,703
[45] Date of Patent: Jan. 23, 1996

[54] HYDRONIC COOLING OF PARTICLE ACCELERATOR WINDOW

[75] Inventors: Joseph R. Lovin, Greer; David S. Shevick, Taylors, both of S.C.

[73] Assignee: W. R. Grace & Co.-Conn., Duncan, S.C.

[21] Appl. No.: 300,689

[22] Filed: Sep. 2, 1994

Related U.S. Application Data

[63] Continuation of Ser. No. 955,529, Oct. 1, 1992, abandoned.

[51] Int. Cl.$^6$ .............................. H01J 7/18; H01J 37/30
[52] U.S. Cl. ....................... 250/492.3; 313/420
[58] Field of Search ........................... 250/492.3, 492.1; 313/420

[56] References Cited

U.S. PATENT DOCUMENTS

| | | | |
|---|---|---|---|
| 2,670,440 | 2/1954 | Gordon et al. | 250/492.3 |
| 2,722,620 | 11/1955 | Gale | 250/492.3 |
| 2,737,593 | 3/1956 | Robinson | 250/492.3 |
| 3,105,916 | 10/1963 | Marker et al. | 313/33 |
| 3,440,466 | 4/1969 | Calvin et al. | 250/492.3 |
| 3,501,391 | 3/1970 | Smith et al. | 250/492.3 |
| 3,536,951 | 10/1970 | De Sola Mosely | 250/492.3 |
| 3,780,305 | 12/1973 | Free | 250/492.3 |
| 4,112,307 | 9/1978 | Föll et al. | 250/492.3 |
| 4,281,251 | 7/1981 | Thompson et al. | 250/492.3 |
| 4,409,511 | 10/1983 | Loda et al. | 313/34 |
| 4,601,331 | 7/1986 | Kessler, Jr. et al. | 165/104.33 |
| 4,642,244 | 2/1987 | Trip, III et al. | 250/492.3 |
| 4,983,849 | 1/1991 | Thompson et al. | 250/492.3 |
| 4,985,635 | 1/1991 | Inokuti et al. | 250/492.3 |
| 5,120,972 | 6/1992 | Rangwalla et al. | 250/492.3 |
| 5,194,742 | 3/1993 | Avnery et al. | 250/492.3 |

FOREIGN PATENT DOCUMENTS 679089  7/1981  U.S.S.R. .

OTHER PUBLICATIONS

The Cool Times Noren Products Ref. Inc.
Colwell et al. "Performance of a Heat Pipe in a Microwave Field" Journal of Microwave Power 19(4), 1975, pp. 369–390.
Bassett et al. "High Power Microwave Window Design" Microwave Symposium, 1974, pp. 145–147.

*Primary Examiner*—Jack I. Berman
*Assistant Examiner*—Kiet T. Nguyen

[57] ABSTRACT

A novel electron beam apparatus window having improved cooling associated therewith, which is in the form of heat pipes located on the window of such apparatus for the cooling of such window by such heat pipes, whereby the heat pipes eliminate the need for air cooling and thus eliminate the production of ozone.

12 Claims, 3 Drawing Sheets

HYDRONIC COOLING OF PARTICLE ACCELERATOR WINDOW

This application is a continuation of application Ser. No. 955,529 filed on Oct. 1, 1992, now abandoned.

BACKGROUND OF THE INVENTION

This invention relates generally to the art of electron beam accelerators and more particularly to the art of cooling such electron beam accelerators.

Electron beam accelerators are used in a variety of environments. The most readily known environment is that of cathode ray tubes which in and of themselves have an extremely diverse variety of applications.

While cathode ray tubes maintain accelerated electrons within the environment of the tube enclosure, applications exist for electron accelerators where the electrons must pass through a window for further utilization. Examples of this are applications such as crosslinking and grafting of polymeric materials, the curing of coatings and inks, the pasteurization of food stuffs or the sterilization of medical products wherein the electrons pass through a thin foil window to reach the product treatment area.

Windows utilized in conventional electron beam accelerators in such applications are generally formed of a foil which is reasonably transparent to an electron beam. Generally such foils are formed of titanium or titanium alloys that are very thin, e.g. approximately 0.4 to 1.5 mils in thickness. In particular, a preferred alloy is formed of 96% (weight percent) titanium with 3% aluminum and 1% vanadium.

When such windows are contacted by the accelerated electrons, a significant portion of the electron energy is imparted to the window resulting in heating thereof. This heat must be removed from the thin foil window or the window will overheat and melt resulting in catastrophic failure of the electron beam accelerator.

Currently such windows are cooled by one of two methods. Water cooled support structures which are either ribbed or perforated cool the window by conduction. Such conduction cooling, however, has not been totally satisfactory since the windows have relatively short lives.

A more effective method of window cooling utilizes a high velocity jet of air which passes over the exterior window surface. Windows cooled in this manner have long service lives, but there is a problem associated with the production of ozone when such air is irradiated by the electrons passing therethrough.

There is thus a significant need for improvement with regard to the cooling of electron beam accelerator windows.

SUMMARY OF THE INVENTION

It is thus an object of this invention to provide a novel electron beam apparatus window having improved cooling associated therewith.

It is further an object of this invention to provide such an improvement which reduces or eliminates the air available for ionization during the cooling of such windows.

These as well as other objects are accomplished by an improvement to an electron beam accelerator in the form of heat pipes located on the window structures of such a generator for the cooling of such window by such heat pipes. The heat pipes eliminate the need for air cooling and thus reduce or eliminate the production of ozone

DETAILED DESCRIPTION

In accordance with this invention, it has been found that the window of an electron beam accelerator may be cooled by the placement thereon of heat pipes for the conduction of heat away therefrom. It is most surprising in accordance with this invention that heat pipes function without deterioration in the environment of an electron beam accelerator. Various other advantages and features will become apparent from a reading of the following description given with reference to the various figures of drawing.

Figure 1:
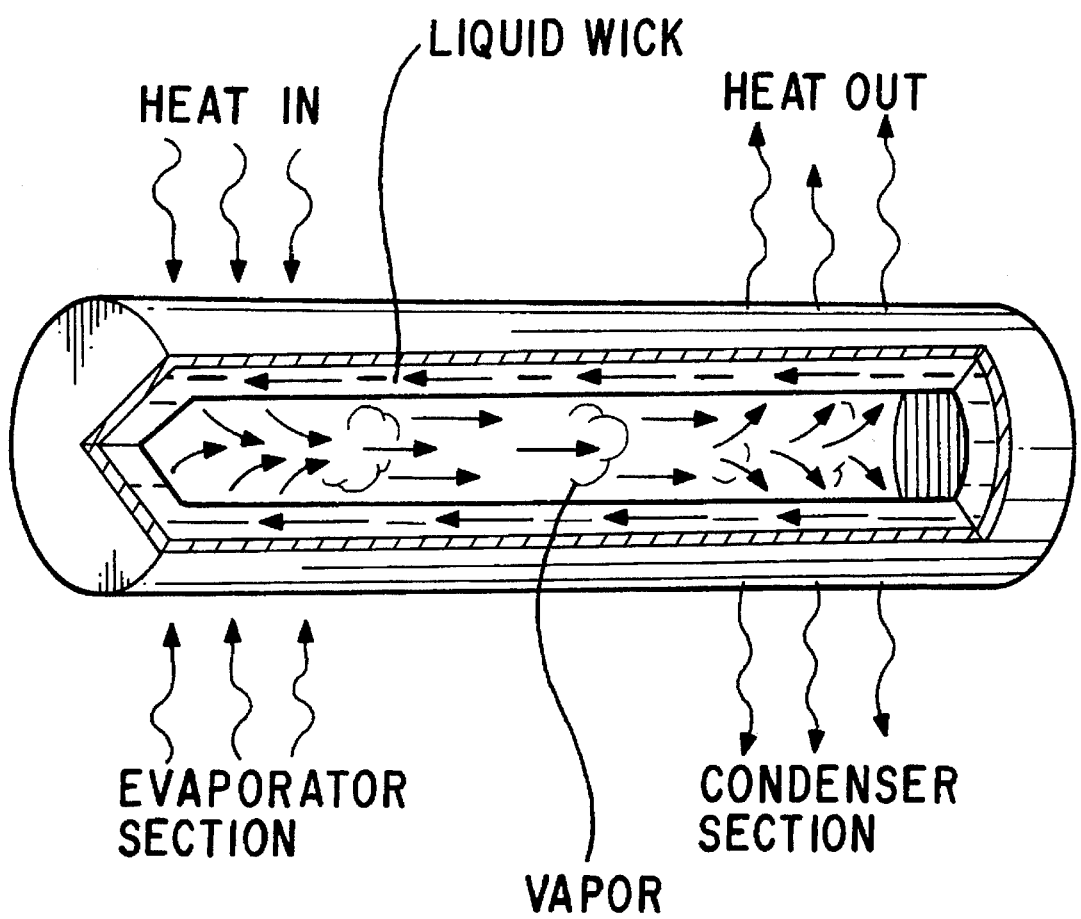
FIG. 1 of the drawings illustrates schematically the operation of a heat pipe.

Heat pipes have been utilized in a variety of applications since their inception. They have been most utilized in the art of injection molding but also utilized in the nuclear reactor art. As used herein and shown schematically in FIG. 1, a heat pipe is generally a hollow tube having a volatile substance therein. The heat pipe is normally formed of thermally conductive material and upon placement of the tube within a heat environment, the volatile liquid within the heat pipe vaporizes and absorbs the heat energy from the portion of the heat pipe subjected to the heat load. This causes the liquid at that point to boil and enter a vapor state. When that happens, the liquid picks up the latent heat of vaporization in passing from the liquid to vapor state. The gas which then has a higher pressure moves toward the center of the sealed container and away from the heat source to a cooler location where it is condensed by external means of cooling. When the gas is condensed, it gives up the latent heat of vaporization. The liquid medium is then returned toward the heat source through the heat pipe wick.

The heat pipe thus functions to transfer heat from the input to output end of the heat pipe with effective thermal conductivities many thousands of times that of copper heat sinks. For example, a heat pipe is described in U.S. Pat. No. 4,601,331 which utilizes a heat pipe in the environment of a microwave tube collector. Such patent is hereby incorporated by reference.

Figure 2:
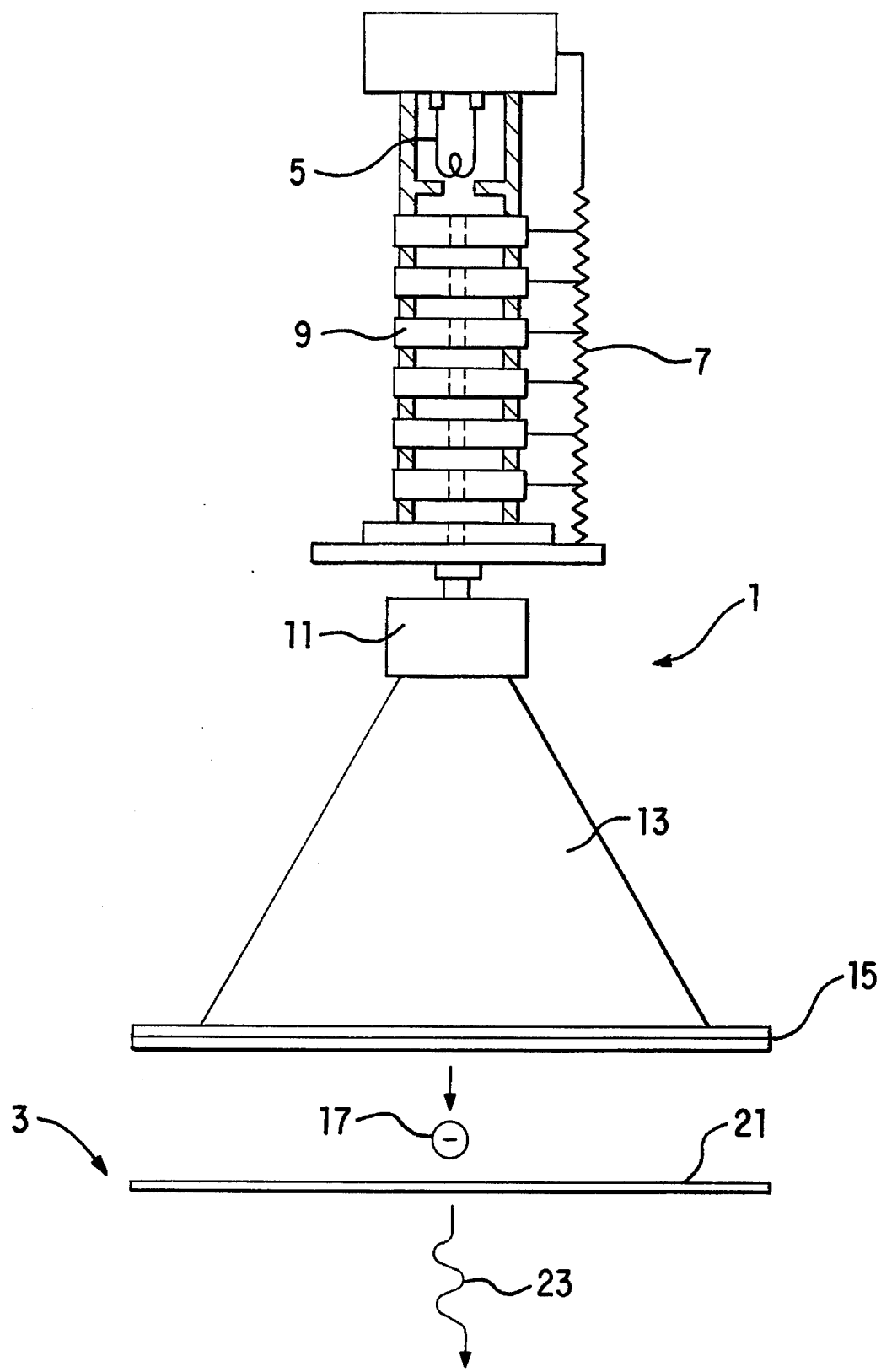
FIG. 2 of the drawings illustrates schematically an electron beam accelerator in association with an x-ray target or product to be irradiated.

FIG. 2 of the drawings illustrates an electron beam accelerator and/or x-ray generator of the type applicable to the current invention. Referring to FIG. 2 of the drawings, there is illustrated an electron beam accelerator 1 and an x-ray generator 3. The electron beam accelerator generally has a filament 5 from which electrons are emitted and passed through a high voltage divider network 7 through a plurality of anodes 9 to arrive in a scan coil assembly 11. In passing through the scan coil assembly, the electrons are scanned through a scanning horn 13 to contact a window 15 such as that described above. An electron 17 is illustrated as having passed through the window and headed toward a metal x-ray target 21 or product to be irradiated.

After traversing through the window the high speed electrons interact with the stream of air being used to cool the window resulting in ionization of the air molecules and consequently the formation of ozone and $NO_x$ products.

Figure 3:
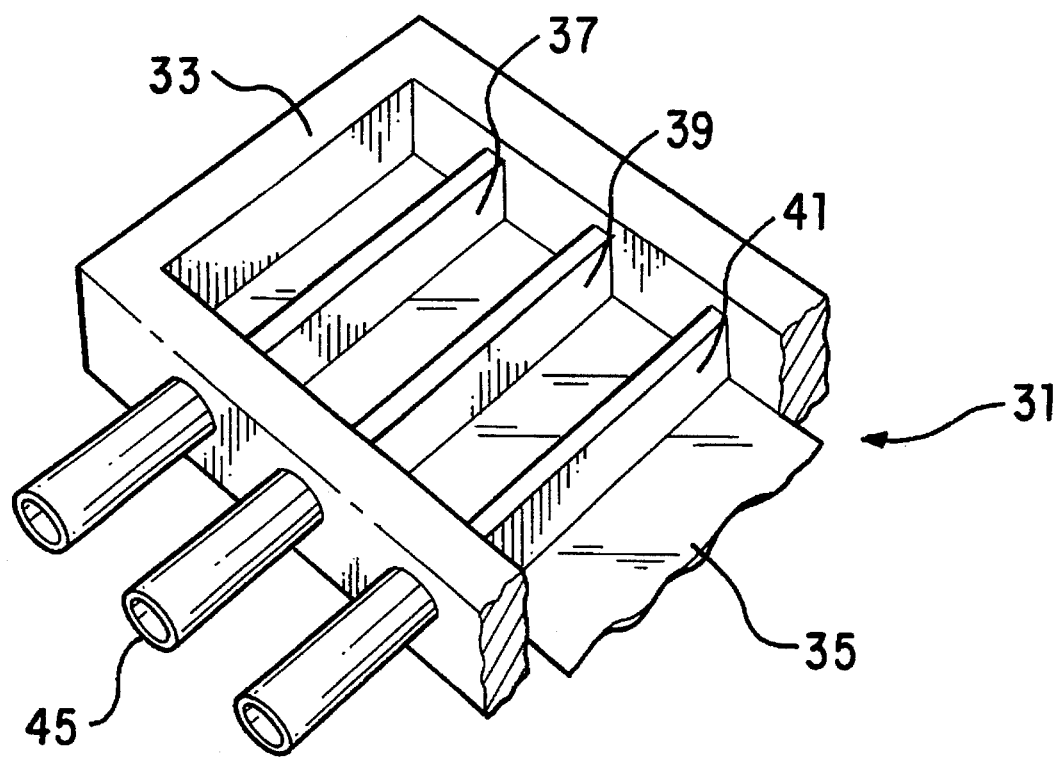
FIG. 3 of the drawings is an isometric view of an electron beam accelerator window assembly in accordance with this invention.

Referring to FIG. 3 of the drawings, a window assembly 31 is illustrated having a window mounting bracket 33, foil window 35 and a plurality of heat pipes illustrated here as 37, 39 and 41. Heat pipes 37, 39 and 41 rest upon window 35 for the conducting of heat away therefrom. There is illustrated also as a part of the window assembly 31, external cooling means 45 which are preferably water cooling for the heat pipes 37, 39 and 41.

A preferred heat pipe for utilization with this invention is a heat pipe from Noren Company of Menlow Park, Calif., which utilizes either mercury or water as the volatile liquid. Surprisingly, both have been found to operate in the environment of the electron accelerator.

One of the advantages associated with the use of heat pipes for cooling an electron window is that the entire electron beam x-ray generator or product irradiation chamber may be isolated in nitrogen and generally the entire environment is isolated except for the cooling water. Therefore, there are no adverse affects to the environment associated with ozone production. The generally inert surrounding of nitrogen also provides for the likelihood of a longer life of all equipment in that environment.

It is thus seen that this invention provides a significant improvement in the cooling of electron beam accelerator windows. It further seen that this improvement eliminates the production of ozone which has heretofore been associated with electron beam accelerators. As many variations become apparent to those of skill in the art from a reading of the foregoing description, such variations are embodied within the spirit and scope of this invention as defined by the following appended claims.

That which is claimed:

1. A method of irradiating an article, comprising the steps of:
   providing an electron beam accelerator, said accelerator comprising a window, a target region, and a heat pipe for cooling the window; wherein said heat pipe comprising a hollow tube having an evaporator section in contact with the window and a condenser section, a volatile liquid in said hollow tube, and a wick;
   irradiating an article in the target region;
   cooling the window while irradiating the article; and
   providing an inert gas to the target region during the irradiating to substantially decrease ozone production.

2. The method of claim 1, wherein the article comprises a polymeric material.

3. The method of claim 2, wherein the inert gas is nitrogen.

4. The method of claim 1, wherein the article comprises a coating.

5. The method of claim 1, wherein the article comprises an ink.

6. The method of claim 5, wherein the inert gas is nitrogen.

7. The method of claim 4, wherein the inert gas is nitrogen.

8. A method of irradiating an article, comprising the steps of:
   providing an electron beam accelerator, said accelerator comprising a particle accelerator window, a target region, and a plurality of heat pipes, each of said heat pipes comprising a hollow tube having an evaporator section in contact with the window and a condenser section, a volatile liquid in said hollow tube, and a wick;
   irradiating an article in the target region and thereby causing the particle accelerator window to heat, thereby heating the liquid and converting the liquid to a vapor to thereby cool the particle accelerator window;
   condensing the vapor to reform the liquid;
   returning the reformed liquid to the evaporator section of the particle accelerator through the wick; and
   providing an inert gas to the target region during the irradiating to substantially decrease ozone production.

9. The method of claim 8, wherein the article comprises a polymeric material.

10. The method of claim 9, wherein the inert gas is nitrogen.

11. The method of claim 8, wherein the article comprises a coating.

12. The method of claim 8, wherein the article comprises an ink.

* * * * *